(12) United States Patent
Reader

(10) Patent No.: US 12,187,716 B2
(45) Date of Patent: Jan. 7, 2025

(54) TYK2 KINASE INHIBITORS

(71) Applicant: SAREUM LIMITED, Cambridgeshire (GB)

(72) Inventor: John Charles Reader, Cambridgeshire (GB)

(73) Assignee: SAREUM LIMITED, Cambridgeshire (GB)

( * ) Notice: Subject to any disclaimer, the term of this patent is extended or adjusted under 35 U.S.C. 154(b) by 945 days.

(21) Appl. No.: 17/283,151

(22) PCT Filed: Oct. 7, 2019

(86) PCT No.: PCT/EP2019/077118
§ 371 (c)(1),
(2) Date: Apr. 6, 2021

(87) PCT Pub. No.: WO2020/074461
PCT Pub. Date: Apr. 16, 2020

(65) Prior Publication Data
US 2021/0387981 A1    Dec. 16, 2021

(30) Foreign Application Priority Data
Oct. 8, 2018    (GB) ...................................... 1816369

(51) Int. Cl.
*C07D 417/12*    (2006.01)

(52) U.S. Cl.
CPC .................................. *C07D 417/12* (2013.01)

(58) Field of Classification Search
CPC ..... C07D 417/12; C07D 263/48; A61P 37/00; A61P 29/00; A61K 31/541
See application file for complete search history.

(56) References Cited

U.S. PATENT DOCUMENTS

| | | |
|---|---|---|
| 7,125,891 B2 | 10/2006 | Breslin et al. |
| 8,378,095 B2 | 2/2013 | Reader et al. |
| 8,624,036 B2 | 1/2014 | Allegretti et al. |
| 8,921,544 B2 | 12/2014 | Reader et al. |
| 9,187,465 B2 | 11/2015 | Reader et al. |
| 10,882,829 B2 | 1/2021 | Reader |
| 11,154,539 B2 | 10/2021 | Reader |
| 11,673,870 B2 | 6/2023 | Reader |
| 2011/0166129 A1 | 7/2011 | Machacek et al. |
| 2013/0102592 A1 | 4/2013 | Reader et al. |
| 2013/0143915 A1 | 6/2013 | Ellard et al. |
| 2013/0231340 A1* | 9/2013 | Reader .................. C07D 263/48 |
| 2015/0018367 A1 | 1/2015 | Reader |
| 2021/0401809 A1 | 12/2021 | Reader |
| 2023/0159473 A1 | 5/2023 | Reader et al. |

FOREIGN PATENT DOCUMENTS

| | | |
|---|---|---|
| DE | 2301030 | 2/1974 |
| DE | 19653355 A1 | 6/1998 |
| DK | 200600313 L | 3/2006 |
| EP | 2634185 A1 | 9/2013 |
| GB | 1374345 | 11/1974 |
| GB | 1497536 | 1/1978 |
| JP | 6310767 A | 1/1988 |
| RU | 2011114992 A | 10/2012 |
| SU | 623518 | 9/1978 |
| WO | 2001058890 A1 | 8/2001 |
| WO | 0200649 A1 | 1/2002 |
| WO | 2004005283 A1 | 1/2004 |
| WO | 2005040139 A2 | 5/2005 |
| WO | 2006095159 A1 | 9/2006 |
| WO | 2007043400 A1 | 4/2007 |
| WO | 2007131953 A1 | 11/2007 |

(Continued)

OTHER PUBLICATIONS

International Search Report and Written Opinion in International Application No. PCT/EP2019/077118. Dec. 9, 2019.
Search Report in GB Application No. 1816369.1. Mar. 28, 2019.
Argiriadi et al., "Enabling Structure-Based Drug Design of Tyk2 Through Co-Crystallization with a Stablilizing Aminoindazole Inhibitor", BMC Structural Biology, Biomed Central Ltd., London GB, vol. 12, No. 1., p. 22 (11 pages) Sep. 20, 2012.
Lykkeberg et al., "Preparation of Some 2,4-Disubstituted Imidazole-5-Carboxamides by Thermolysis of β-Substituted α-(1-Tetrazolyl) Acrylamides", Acta Chemica Scandinavica, Series B: Organic Chemistry and Biochemistry. B29(7), pp. 793-795. 1975.

(Continued)

*Primary Examiner* — Joseph K McKane
*Assistant Examiner* — David M Shim
(74) *Attorney, Agent, or Firm* — Heslin Rothenberg Farley & Mesiti P.C.

(57) ABSTRACT

The invention provides compounds of the formula (1):

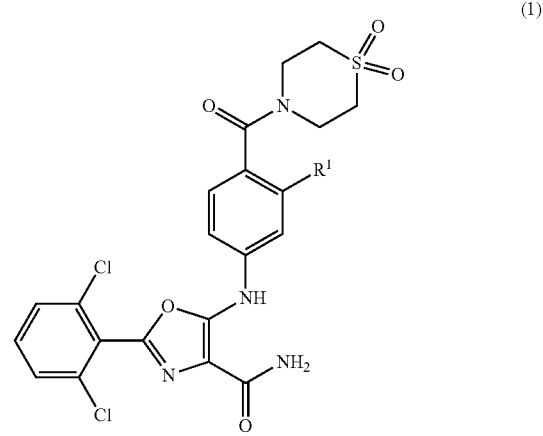

or a salt or tautomer thereof, wherein $R^1$ is hydrogen or fluorine, pharmaceutical compositions containing the compounds and medical uses of the compounds (for example, in the treatment of inflammatory or immune disorders).

20 Claims, No Drawings

(56) References Cited

FOREIGN PATENT DOCUMENTS

| WO | 2008024980 | A2 | 2/2008 |
|---|---|---|---|
| WO | 2008139161 | A1 | 11/2008 |
| WO | 2008156726 | A1 | 12/2008 |
| WO | 2009155156 | A1 | 12/2009 |
| WO | 2010005841 | A1 | 1/2010 |
| WO | 2010011375 | A2 | 1/2010 |
| WO | 2010055304 | A2 | 5/2010 |
| WO | 2011113802 | A2 | 9/2011 |
| WO | 2012000970 | A1 | 1/2012 |
| WO | 2012021611 | A1 | 2/2012 |
| WO | 2013055645 | A1 | 4/2013 |
| WO | 2014074661 | A1 | 5/2014 |
| WO | 2015032423 | A1 | 3/2015 |
| WO | 2016027195 | A1 | 2/2016 |
| WO | 2018073438 | A1 | 4/2018 |

OTHER PUBLICATIONS

Ozaki et al., "Syntheses of 5-Substituted Oxazole-4-Carboxylic Acid Derivatives with Inhibitory Activity on Blood Platelet Aggression", Chem. Pharm. Bull., 31(12), pp. 4417-4424. 1983.

Harrington et al., "VX-680, A Potent and Selective Small-Molecule Inhibitor of the Aurora Kinases, Suppresses Tumor Growth in vivo", Nature Medicine, vol. 10, No. 3, pp. 262-267. Mar. 2004.

Francheti et al., "Synthesis and Antitumor Activity of 2-β-D-Ribofuranosylozazole-4-carbozamide", (Oxazofurin), J. Med. Chem., 33, pp. 2849-2852. 1990.

Jansen et al., Some 4-Substituted Oxazoles, J. Chem. Soc., pp. 405-411. 1961.

Morwick et al. "Evolution of the Trienopyridine Class of Inhibitors of IκB Kinase-β: Part I: Hit-to-Lead Strategies", J. Med. Chem., 49, pp. 2898-2908. 2006.

Spiekermann et al., "The Protein Tyrosine Kinase Inhibitor SU5614 Inhibits FLT3 and Induces Growth Arrest and Apoptosis in AML-Derived Cell Lines Expressing a Constitutively Activated FLT3", Blood, 101(4), pp. 1494-1504. 2003.

Ponomarev et al., Zhurnal Fizicheskoi Khimii, 64(10), pp. 2723-2729 (Chem Abs. 114:100938). 1990.

Works et al., "Inhibition of TYK2 and JAK1 Ameliorates Imiquimod-Induced Psoriasis-like Dermatitis by Inhibiting IL-22 and the IL-23/IL-17 Axis", The Journal of Immunology, vol. 193, pp. 3278-3287. Aug. 25, 2014.

Papp et al., "Phase 2 Trial of Selective Tyrosine Kinase 2 Inhibition in Psoriasis", The New England Journal of Medicine, pp. 1313-1321. Sep. 12, 2018.

* cited by examiner

TYK2 KINASE INHIBITORS

CROSS REFERENCE TO RELATED APPLICATIONS

This application is a U.S. National Phase filing under 35 U.S.C. § 371 of International Application PCT/EP2019/077118, filed Oct. 7, 2019, and published as WO 2020/074461 A1 on Apr. 16, 2020. PCT/EP2019/077118 claims priority from Great Britain patent application number 1816369.1, filed Oct. 8, 2018. The entire contents of each of these prior applications are hereby incorporated herein by reference.

This invention relates to compounds having Janus kinase inhibiting activity, and in particular TYK2 kinase inhibiting activity, pharmaceutical compositions containing them and their use in the treatment of various diseases such as autoimmune diseases.

BACKGROUND OF THE INVENTION

Protein kinases constitute a large family of structurally related enzymes that are responsible for the control of a wide variety of signal transduction processes within the cell (Hardie and Hanks (1995) *The Protein Kinase Facts Book. I and II*, Academic Press, San Diego, CA). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks and Hunter, *FASEB J.*, (1995) 9. 576-596; Knighton, et al., *Science,* (1991) 253, 407-414; Hiles, et al., *Cell,* (1992) 70, 419-429; Kunz, et al., *Cell,* (1993) 73, 585-596; Garcia-Bustos, et al., *EMBO J.,* (1994) 13, 2352-2361).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

The Janus kinase (JAK) family is a family of intracellular non-receptor tyrosine kinases, ranging in size from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2. JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's.

Each JAK kinase protein has a kinase domain and a catalytically inactive pseudo-kinase domain. The JAK proteins bind to cytokine receptors through their amino-terminal FERM (Band-4.1, ezrin, radixin, moesin) domains. After the binding of cytokines to their receptors, JAKs are activated and phosphorylate the receptors, thereby creating docking sites for signalling molecules, especially for members of the signal transducer and activator of transcription (STAT) family (Yamaoka et al, 2004. The Janus kinases (Jaks). Genome Biology 5(12): 253).

In mammals, JAK1, JAK2 and TYK2 are ubiquitously expressed. TYK2 activates signal transducer and activator of transcription (STAT)-dependent gene expression and functional responses of interleukin-12, interleukin-23, and type I and III interferon receptors (Papp et al., The New England Journal of Medicine, 12 Sep. 2018, DOI: 10.1056/NEJMoa1806382 and references cited therein) These cytokine pathways are involved in the pathologic processes associated with immune-mediated disorders, including psoriasis, and are reported (Papp et al., idem) to be distinct from responses driven by Janus kinase (JAK) 1 (JAK1), JAK1 and JAK3 in combination, JAK2, or other signalling kinases.

Interleukin-23 (IL-23), composed of two subunits p19 and p40, is considered to be essential for the survival and expansion of Th17 cells which produce pro-inflammatory cytokines such as IL-17A, IL-17F, IL-6 and TNFα (see WO2014/07466 and references cited therein). These cytokines are reported as being critical in mediating the pathobiology of a number of autoimmune diseases including rheumatoid arthritis, multiple sclerosis, inflammatory bowel disease, and lupus.

IL-23 acts through a heterodimeric receptor composed of IL-12R(31 and IL-23R.

IL-12, in addition to the p40 subunit in common with IL-23, contains a p35 subunit and acts through a heterodimeric receptor composed of IL-12R1β and IL-12Rβ2. IL-12 is essential for Th1 cell development and secretion of IFNy, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol, 26: 1217-1221 (1996); Schroder, K. et al., "Interferon-gamma: an overview of signals, mechanisms and functions", J. Leukoc. Biol, 75(2): 163-189 (2004)).

TYK2 associates with the IL-12R(31 subunit in the IL-12 and IL-23 receptors.

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al, "Cutting edge: IL-23 receptor deficiency prevents the development of lupus nephritis in C57BL/6-Ipr/Ipr mice", J. Immunol, 184:4605-4609 (2010); Hong, K. et al, "IL-12, independently of IFN-gamma, plays a crucial role in the pathogenesis of a murine psoriasis like skin disorder", J. Immunol, 162:7480-7491 (1999); Hue, S. et al, "Interleukin-23 drives innate and T cell-mediated intestinal inflammation", J. Exp. Med., 203:2473-2483 (2006); Cua, D. J. et al., "Interleukin-23 rather than interleukin-12 is the critical cytokine for autoimmune inflammation of the brain", Nature, 421:744-748 (2003); Murphy, C. A. et al., "Divergent pro- and anti-inflammatory roles for IL-23 and IL-12 in joint autoimmune inflammation", J. Exp. Med, 198: 1951-1957 (2003)).

The role of TYK2 in the biological response to cytokines has been characterized using a mutant human cell line that was resistant to the effects of Type I interferons (IFNs) and by demonstrating that IFNα responsiveness could be restored by genetic complementation of TYK2 (Velazquez et al, 1992. Cell 70, 313-322). Further in vitro studies have implicated TYK2 in the signalling pathways of multiple other cytokines involved in both innate and adaptive immunity. However, analysis of TYK2$^{-/-}$ mice revealed less profound immunological defects than were anticipated (Karaghiosoff et al, 2000. Immunity 13, 549-560; Shimoda et al, 2000. Immunity 13, 561-671). Surprisingly, TYK2 deficient mice display merely reduced responsiveness to IFNα/β and signal normally to interleukin 6 (IL-6) and interleukin 10 (IL-10), both of which activate TYK2 in vitro. In contrast, TYK2 was shown to be essential for IL-12 signalling with the absence of TYK2 resulting in defective STAT4 activation and the failure of T cells from these mice to differentiate into IFNγ-producing Th1 cells. Consistent with the involvement of TYK2 in mediating the biological effects of Type I IFNs and IL-12, TYK2$^{-/-}$ mice were more susceptible to viral and bacterial infections.

The first patient with an autosomal recessive TYK2 deficiency was described by Minegishi et al, 2006. Immunity 25, 745-755. The homozygous deletion of four base pairs (GCTT at nucleotide 550 in the TYK2 gene) and consequent frameshift mutation in the patient's coding DNA introduced a premature stop codon and resulted in the truncation of the TYK2 protein at amino acid 90. The phenotype of this null mutation in human cells was much more severe than predicted by the studies in murine cells lacking TYK2. The patient displayed clinical features reminiscent of the primary immunodeficiency hyper-IgE syndrome (HIES) including recurrent skin abscesses, atopic dermatitis, highly elevated serum IgE levels and susceptibility to multiple opportunistic infections.

Contrary to reports in TYK2$^{-/-}$ mice, signalling by a wide variety of cytokines was found to be impaired thus highlighting non-redundant roles for human TYK2 in the function of Type I IFNs, IL-6, IL-10, IL-12 and IL-23. An imbalance in T helper cell differentiation was also observed, with the patient's T cells exhibiting an extreme skew towards the development of IL-4 producing Th2 cells and impaired Th1 differentiation. Indeed, these cytokine signalling defects could be responsible for many of the clinical manifestations described, for example atopic dermatitis and elevated IgE levels (enhanced Th2), increased incidence of viral infections (IFN defect), infection with intracellular bacteria (IL-12/Th1 defect) and extracellular bacteria (IL-6 and IL-23/Th17 defect).

Seven further TYK2-deficient patients from five families and four different ethnic groups were identified by Kreins et al., pages 1-22, The Journal of Experimental Medicine, published 24 Aug. 2015. These patients were homozygous for one of five null mutations. By comparing the data obtained by Minegishi et al. with the data obtained for the seven further TYK2-deficient patients, Kreins et al. concluded that the core clinical phenotype of TYK2 deficiency is mycobacterial and/or viral infections, caused by impaired responses to IL-12 and IFN-α/β but that impaired IL-6 responses and HIES do not appear to be intrinsic features of TYK2 deficiency in humans.

Emerging evidence from genome-wide association studies suggests that single nucleotide polymorphisms (SNPs) in the TYK2 gene significantly influence autoimmune disease susceptibility.

Less efficient TYK2 variants are associated with protection against systemic lupus erythematosus (SLE) (TYK2 rs2304256 and rsl2720270, Sigurdsson et al, 2005. Am. J. Hum. Genet. 76, 528-537; Graham et al, 2007. Rheumatology 46, 927-930; Hellquist et al, 2009. J. Rheumatol. 36, 1631-1638; Jarvinen et al, 2010. Exp. Dermatol. 19, 123-131) and multiple sclerosis (MS) (rs34536443, Ban et al, 2009. Eur. J. Hum. Genet. 17, 1309-1313; Mero et al, 2009. Eur. J. Hum. Genet. 18, 502-504), whereas predicted gain-of-function mutations increase susceptibility to inflammatory bowel disease (IBD) (rs280519 and rs2304256, Sato et al, 2009. J. Clin. Immunol. 29, 815-825).

It has been reported (see WO2014074661 and references cited therein) that in humans, individuals expressing an inactive variant of TYK2 are protected from multiple sclerosis and possibly other autoimmune disorders, and that genome-wide association studies have shown other variants of TYK2 to be associated with autoimmune disorders such as Crohn's Disease, psoriasis, systemic lupus erythematosus, and rheumatoid arthritis, further demonstrating the importance of TYK2 in autoimmunity.

In support of the involvement of TYK2 in immunopathologic disease processes, it has been shown that B10.D1 mice harbouring a missense mutation in the pseudokinase domain of TYK2 that results in the absence of encoded TYK2 protein are resistant to both autoimmune arthritis (CIA) and experimental autoimmune encephalomyelitis (EAE) (Shaw et al, 2003. PNAS 100, 11594-11599; Spach et al, 2009. J. Immunol. 182, 7776-7783). Furthermore, a recent study showed that TYK2$^{-/-}$ mice were completely resistant to MOG-induced EAE (Oyamada et al, 2009. J. Immunol. 183, 7539-7546). In these mice resistance was accompanied by a lack of CD4 T cells infiltrating the spinal cord, a failure to signal through IL-12R and IL-23R and hence the inability to upregulate encephalitogenic levels of IFNγ and IL-17.

Overexpression of TYK2 kinase has been implicated in the development of some disease states. For example, elevated levels of TYK2 were found in patients suffering from progressive pulmonary sarcoidosis (Schischmanoff et al., *Sarcoidosis Vasc. Diffuse.*, 2006, 23(2), 101-7).

Thus, the available evidence strongly indicates that TYK2 plays essential roles in both innate and adaptive immunity. A lack of TYK2 expression manifests in the attenuated signalling of multiple proinflammatory cytokines and a profound imbalance in T helper cell differentiation. Furthermore, evidence from genetic association studies supports that TYK2 is a shared autoimmune disease susceptibility gene. Taken together, these reasons suggest TYK2 as a target for the treatment of inflammatory and auto-immune diseases.

Several JAK family inhibitors have been reported in the literature which may be useful in the medical field (Ghoreschi et al, 2009. Immunol Rev, 228:273-287). It has been proposed that a selective TYK2 inhibitor that inhibits TYK2 with greater potency than JAK2 may have advantageous therapeutic properties, because inhibition of JAK2 can cause anemia (Ghoreschi et al, 2009. Nature Immunol. 4, 356-360).

Papp et al. (The New England Journal of Medicine, 12 Sep. 2018, DOI: 10.1056/NEJMoa1806382) disclose the results obtained in Phase II clinical trials of the oral selective TYK2 inhibitor BMS-986165 in treating psoriasis and concluded that the results indicated a therapeutic benefit.

WO2014/074661 (Bristol-Myers Squibb) discloses a class of pyridazine and triazine amides as TYK2 inhibitors that are useful in the modulation of IL-12 IL-23 and/or IFNα. It is suggested that the compounds will be useful in the treatment of various inflammatory and autoimmune diseases.

WO2016/027195 (Pfizer) discloses a series of aminopyrimidinyl compounds having JAK kinase inhibiting activity, including activity ageist TYK2 kinase.

WO2012/000970 (Cellzome) discloses a series of triazolopyridines as TYK2 kinase inhibitors. WO2011/113802 (Roche) discloses a series of imidazopyridines as TYK2 kinase inhibitors. The properties of JAK kinases and their relevance as therapeutic targets are also disclosed in WO2008/156726, WO2009/155156, WO2010/005841 and WO2010/011375, all in the name of Merck.

WO2010/055304 and EP2634185 (both in the name of Sareum) disclose a family of substituted oxazole carboxamides for use in the prophylaxis or treatment of autoimmune diseases and in particular multiple sclerosis. The compounds disclosed in WO2010/055304 are described as being FLT3 kinase inhibitors. The kinase inhibiting effect of oxazole carboxamides is also disclosed in International patent application WO2008/139161 (Sareum).

WO2015/032423 (Sareum) discloses the the use of a subset of oxazole carboxamide compounds as TYK2 kinase inhibitors. The compounds are described as being useful in the treatment of inflammatory and immunological disorders such as autmoimmune diseases.

WO2018/073438 (Sareum) discloses the the use of a subset of oxazole carboxamide compounds having TYK2 kinase inhibitory activity for use in treating T-cell lymphoblastic leukemias and cancers (such as hematopoietic cancers) which depend on the Janus kinase TYK2 for cancer cell survival.

Particular compounds disclosed in WO2015/032423 and WO2018/073438 include 2-(2-chloro-6-fluoro-phenyl)-5-[4-(morpholine-4-carbonyl)-phenylamino]-oxazole-4-carboxylic acid amide (Compound A) and 2-(2,6-dichlorophenyl)-5-[4-(morpholine-4-carbonyl)-phenylamino]-oxazole-4-carboxylic acid amide (Compound B).

The Invention

The present invention relates to a small group of oxazole carboxamides that have improved activity against and selectivity for TYK2 kinase and improved pharmacokinetic properties compared to compounds disclosed in WO2015/032423 and WO2018/073438 and in particular the abovementioned Compound A and Compound B.

Accordingly, in a first embodiment (Embodiment 1.1), the invention provides a compound having the formula (1):

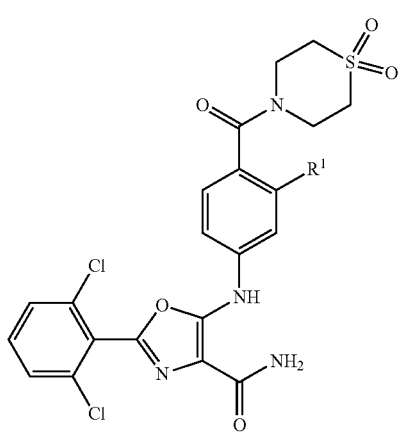

(1)

or being a salt or tautomer thereof; wherein $R^1$ is hydrogen or fluorine.

Particular compounds of the invention are set out in Embodiments 1.2 to 1.9 below.

1.2 A compound according to Embodiment 1.1, wherein $R^1$ is hydrogen; the compound having the formula (2):

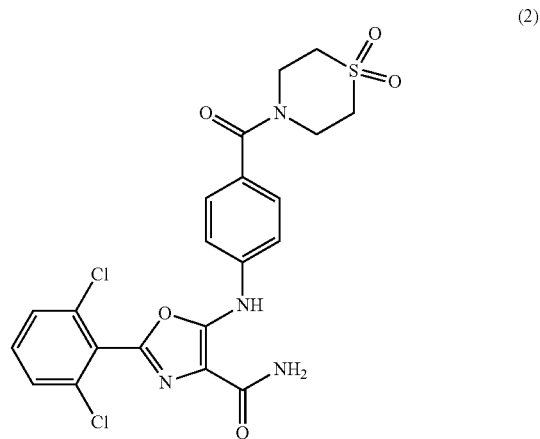 [SMILES: NC(=O)c1nc(-c2c(Cl)cccc2Cl)oc1Nc1ccc(C(=O)N2CCS(=O)(=O)CC2)cc1]

(2)

or being a salt or tautomer thereof.

1.3 A compound according to Embodiment 1.1 wherein $R^1$ is fluorine; the compound having the formula (3):

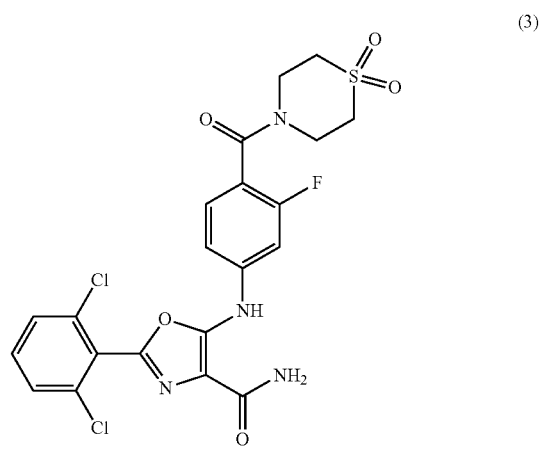 [SMILES: NC(=O)c1nc(-c2c(Cl)cccc2Cl)oc1Nc1ccc(C(=O)N2CCS(=O)(=O)CC2)c(F)c1]

(3)

or being a salt or tautomer thereof.

The compounds of formulae (1), (2) and (3) contain oxazole and aniline sub-units, both of which are only weakly basic. The compounds are therefore typically provided in a non-salt form rather than as salts. Accordingly, in a further embodiment (Embodiment 1.4), the invention provides a compound according to any one of Embodiments 1.1 to 1.3 wherein the compound is in a non-salt form.

In certain circumstances, acid salts may be formed with strong acids such as hydrochloric, sulphuric and phosphoric acid but it is envisaged that such salts will typically be unstable. Where salts can be formed, they can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Where salts can be formed, they may be pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Isotopes

The compounds for use according to the invention as defined in any one of Embodiments 1.1 to 1.4 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise.

The isotopes may be radioactive or non-radioactive. In one embodiment of the invention (Embodiment 1.5), the compound according to any one of Embodiments 1.1 to 1.4 contains no radioactive isotopes. Such compounds are preferred for therapeutic use. In another embodiment (Embodiment 1.6), however, the compound of any one of Embodiments 1.1 to 1.4 may contain one or more radioisotopes. Compounds containing such radioisotopes may be useful in a diagnostic context.

Solvates

Compounds for use as defined in any one of Embodiments 1.1 to 1.6 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

Accordingly, in further embodiments 1.7 and 1.8, the invention provides:

1.7 A compound according to any one of Embodiments 1.1 to 1.6 wherein the compound is in the form of a solvate.

1.8 A compound according to Embodiment 1.7 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, IN, USA, 1999, ISBN 0-967-06710-3.

Alternatively, rather than existing as a hydrate, the compound of the invention may be anhydrous. Therefore, in another embodiment (Embodiment 1.9), the compound as defined in any one of Embodiments 1.1 to 1.6 is in an anhydrous form.

Biological Activity

Compounds of the formulae (1), (2) and (3) as defined in Embodiments 1.1 to 1.9 are potent and selective inhibitors of TYK2 kinase. The TYK2 kinase-inhibiting activities of the compounds can be determined using the assays described in the Examples below.

Experimental data obtained for the compounds (2) and (3) demonstrate that the compounds of the invention have significant advantages over the structurally most similar compound (Compound B) in WO2015/032423. Thus, both compounds (2) and (3) are more active than the closest known compound (Compound B) in the TYK2 kinase inhibition assay and both have greater selectivity for TYK2 versus JAK1, JAK2 and JAK3 kinases than Compound B. Moreover, Compounds (2) and (3) have a reduced hERG liability compared to prior art comparative Compound B. Furthermore, in the hepatocyte stability assays, Compounds (2) and (3) showed a reduced rate of clearance and a consequently longer half life than comparative Compound B.

Taken together, the data indicate that Compounds (2) and (3) are not only more potent and more selective TYK2 kinase inhibitors than comparative Compound B but that, moreover, they have better pharmacokinetic properties than Compound B.

The TYK2 kinase-inhibiting activities of the compounds can be made use of in various methods of treating diseases where TYK2 plays a part in the development or progression of the disease. The various uses of the compounds typically involve bringing the compounds into contact with a TYK2 kinase. The inhibition of the TYK2 kinase may take place either in vitro or in vivo.

Accordingly, in further embodiments, the invention provides:

2.1 A method of inhibiting a TYK2 kinase, which method comprises bringing into contact with the TYK2 kinase an effective TYK2 kinase-inhibiting amount of a compound as defined in any one of Embodiments 1.1 to 1.9.

2.2 A method according to Embodiment 2.1 wherein the inhibition of the TYK2 kinase takes place in vitro.

2.3 A method according to Embodiment 2.1 wherein the inhibition of the TYK2 kinase takes place in vivo.

2.4 A compound as defined in any one of Embodiments 1.1 to 1.9 for use as an inhibitor of TYK2 kinase.

2.5 A compound as defined in any one of Embodiments 1.1 to 1.9 for use in medicine.

The inhibition of TYK2 kinase preferably takes place in vivo as part of a therapeutic treatment of a disease or condition in which TYK2 kinase is implicated.

The compounds of the invention are selective TYK2 inhibitors and are considerably more active against TYK2 than JAK2 and JAK3 kinases. The compounds have relatively poor activity against a wide range of other kinases and, in particular, kinases that are generally recognised as targets for anti-cancer therapy. Thus, for example, the compounds have relatively little activity against Chk1 kinase, Aurora kinases, PKB (Akt) kinase and cyclin dependent kinases (CDK kinases) which are involved in cell cycle progression. A lack of activity against kinases typically considered to be anti-cancer targets is beneficial in compounds that may be used in chronic treatment of inflammatory and autoimmune diseases for example.

It is envisaged on the basis of their TYK2 inhibiting activity that the compounds of the invention will be useful in treating at least some of the diseases and disorders discussed below, including inflammatory diseases or conditions, immunological diseases or conditions, autoimmune diseases, allergic diseases or disorders, transplant rejections (allograft transplant rejections); Graft-versus host disease; treating sepsis and septic shock.

In the context of the present invention, an autoimmune disease is a disease which is at least partially provoked by an immune reaction of the body against its own components, for example proteins, lipids or DNA. Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), coeliac disease, psoriasis, inflammatory bowel disease (IBD), lupus nephritis (an inflammation of the kidney) and ankylosing spondylitis. Examples of non-organ-specific autoimmune disorders are rheumatoid arthritis, multiple sclerosis, systemic lupus erythematosus, and myasthenia gravis. Type I diabetes ensues from the selective aggression of autoreactive T-cells against insulin secreting beta-cells of the islets of Langerhans. Other inflammatory or immune diseases and disorders, sufferers from which may benefit from treatment with the compounds of the invention include skin inflammation due to radiation exposure; asthma; allergic inflammation; chronic inflammation; an inflammatory ophthalmic disease; dry eye syndrome (DES, also known as keratoconjunctivitis sicca or dysfunctional tear syndrome); uveitis (e.g. chronic progressive or relapsing forms of non-infectious uveitis); alopecia areata; primary biliary cirrhosis; and systemic sclerosis;

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361).

Inflammatory bowel disease (IBD) is characterized by a chronic relapsing intestinal inflammation. IBD is subdivided into Crohn's disease and ulcerative colitis phenotypes. Crohn's disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn's disease or ulcerative colitis cannot be made and are designated 'indeterminate colitis'. Both diseases include extraintestinal inflammation of the skin, eyes, or joints. Neutrophil-induced injuries may be prevented by the use of neutrophil migration inhibitors (Asakura et al., 2007, World J. Gastroenterol. 13(15):2145-9).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schon et al, 2005, New Engl. J. Med. 352: 1899-1912).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive CD4+ memory cells (D'Cruz et al, 2007, Lancet 369(9561):587-596).

Transplant rejection (allograft transplant rejection) includes, without limitation, acute and chronic allograft rejection following for example transplantation of kidney, heart, liver, lung, bone marrow, skin and cornea. It is known that T cells play a central role in the specific immune response of allograft rejection. Hyperacute, acute and chronic organ transplant rejection may be treated. Hyperacute rejection occurs within minutes of transplantation. Acute rejection generally occurs within six to twelve months of the transplant. Hyperacute and acute rejections are typically reversible where treated with immunosuppressant agents. Chronic rejection, characterized by gradual loss of organ function, is an ongoing concern for transplant recipients because it can occur any time after transplantation.

Graft-versus-host disease (GVDH) is a major complication in allogeneic bone marrow transplantation (BMT). GVDH is caused by donor T cells that recognize and react to recipient differences in the histocompatibility complex system, resulting in significant morbidity and mortality.

Pulmonary sarcoidosis is a relatively rare inflammatory disorder of unknown cause, but which has been shown to be associated with elevated levels of TYK2, and which typically develops in adults of 20 to 50 years of age. Pulmonary sarcoidosis is characterised by small lumps, or granulomas in the lungs, which generally heal and disappear on their own.

However, for those granulomas that do not heal, the tissue can remain inflamed and become scarred, or fibrotic. Pulmonary sarcoidosis can develop into pulmonary fibrosis, which distorts the structure of the lungs and can interfere with breathing.

Accordingly, in further embodiments, the invention provides:

2.6 A method of treating a disease or condition in a subject in need thereof, wherein the disease or condition is selected from an autoimmune disease, an inflammatory disease or condition, an immunological disease or condition, an allergic disease or disorder, a transplant rejection and Graft-versus host disease, or a disease or condition selected from sepsis and septic shock, wherein the disease or condition is susceptible to TYK2 inhibition, which method comprises administering to the subject an effective TYK2 inhibiting amount of a compound as defined in any one of Embodiments 1.1 to 1.9.

2.7 A compound as defined in any one of Embodiments 1.1 to 1.9 for use in the treatment of a disease or condition wherein the disease or condition is selected from an autoimmune disease, an inflammatory disease or condition, an immunological disease or condition, an allergic disease or disorder, a transplant rejection and Graft-versus host disease; or for use in the treatment of sepsis or septic shock, wherein the disease or condition is susceptible to TYK2 inhibition.

2.8 The use of a compound as defined in any one of Embodiments 1.1 to 1.9 for the manufacture of a medicament for the treatment of a disease or condition selected from an autoimmune disease, an inflammatory disease or condition, an immunological disease or condition, an allergic disease or disorder, a transplant rejection and Graft-versus host disease; or for use in the treatment of sepsis or septic shock, wherein the disease or condition is susceptible to TYK2 inhibition.

2.9 A method of treating an autoimmune disease in a subject in need thereof, which method comprises administering to the subject an effective TYK2 inhibiting amount of a compound as defined in any one of Embodiments 1.1 to 1.9, so as to inhibit TYK2 kinase in the subject and thereby block or reduce the extent of an inflammatory process associated with the autoimmune disease.

2.10 A compound as defined in any one of Embodiments 1.1 to 1.9, for use in a method of treating an autoimmune disease in a subject in need thereof, which method comprises administering to the subject an effective TYK2 inhibiting amount of the said compound, so as to inhibit TYK2 kinase in the subject and thereby block or reduce the extent of an inflammatory process associated with the autoimmune disease.

2.11 The use of a compound as defined in any one of Embodiments 1.1 to 1.9, for the manufacture of a medicament for treating an autoimmune disease in a subject in need thereof by administering to the subject an effective TYK2 inhibiting amount of the said compound, so as to inhibit TYK2 kinase in the subject and thereby block or reduce the extent of an inflammatory process associated with the autoimmune disease.

2.12 A method of treating a disease or condition in a subject in need thereof, wherein the disease or condition is one which is characterized or caused (at least in part) by or associated with overexpression (elevated expression) of TYK2 kinase, which method comprises administering to the subject an effective TYK2 inhibiting amount of a compound of any one of Embodiments 1.1 to 1.9.

2.13 A compound as defined in any one of Embodiments 1.1 to 1.9, for use in treating a disease or condition in a subject in need thereof, wherein the disease is one which is characterized or caused (at least in part) by or associated with overexpression (elevated expression) of TYK2 kinase.

2.14 A method, compound for use or use according to any one of Embodiments 2.6 to 2.13 wherein the disease or condition is an autoimmune disease.

2.15 A method, compound for use or use according to any one of Embodiments 2.6 to 2.13 wherein the disease or condition is an autoimmune disease other than multiple sclerosis.

2.16 A method, compound for use or use according to any one of Embodiments 2.6 to 2.13 wherein the disease or condition is psoriasis.

2.17 A method, compound for use or use according to any one of Embodiments 2.6 to 2.13 wherein the disease or condition is psoriatic arthritis.

2.18 A method according to Embodiment 2.6 wherein the disease or condition is multiple sclerosis.

The activity of the compounds of the invention as TYK2 inhibitors can be measured using the assay set forth in the examples below and the level of activity exhibited by a given compound can be defined in terms of the $IC_{50}$ value. The compounds of the present invention have $IC_{50}$ values against TYK2 kinase of less than 5 nanomolar. Thus, the compound wherein $R^1$ is hydrogen (Compound (2)) has an $IC_{50}$ against TYK2 of 1.9 nanomolar whereas the compound wherein $R^1$ is fluorine (Compound (3)) has an $IC_{50}$ against TYK2 of 4.7 nanomolar.

An advantage of compounds of the invention is that they exhibit selectivity for TYK2 kinase compared to other kinases of the JAK family.

For example, in biochemical assays, the compound wherein $R^1$ is hydrogen (Compound (2)) has approximately 25-fold selectivity for TYK2 compared to JAK2 and 110-fold selectivity for TYK2 compared to JAK3.

The compound where $R^1$ is fluorine (Compound (3)) has approximately 32-fold selectivity for TYK2 compared to JAK2 and 164-fold selectivity for TYK2 compared to JAK3.

The suitability of the compounds for use in treating psoriasis can be determined by testing the effect of the compounds on imiquimod-induced psoriasis-like skin inflammation in mice: see for example Mori et al., Kobe J. Med. Sci., Vol. 62, No. 4, pp. E79-E88, 2016; van der Fits et al., The Journal of Immunology, 2009; 182: 5836-5845; and Lin et al., PLOS ONE| DOI:10.1371/journal-.pone.0137890 Sep. 10, 2015. Thus, imiquimod can be applied topically to mice (for example to an ear of a mouse) to induce psoriasis-like inflammation and scaling, and a comparison made between the levels of inflammation and scaling in mice (or areas of the body of mice) that have also been treated with a compound of the invention or a control containing no imiquimod.

Methods for the Preparation of Compounds of Formula (1)

The compounds of the invention can be prepared by the methods described in the following paragraphs and in the Examples below.

The Compounds of formula (1) can be prepared by the sequence of reactions shown in Scheme 1.

Scheme 1

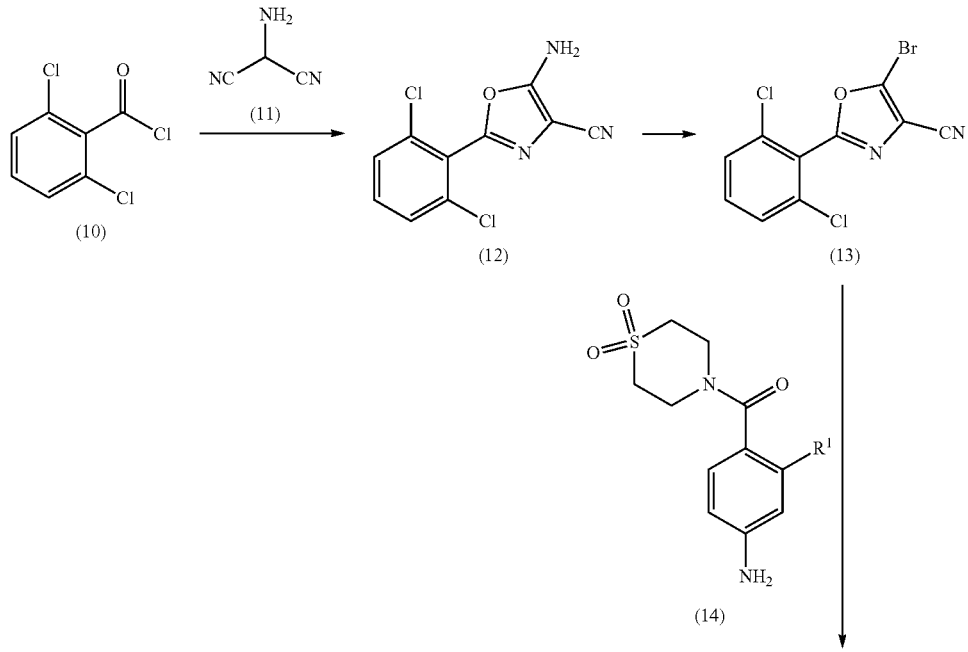

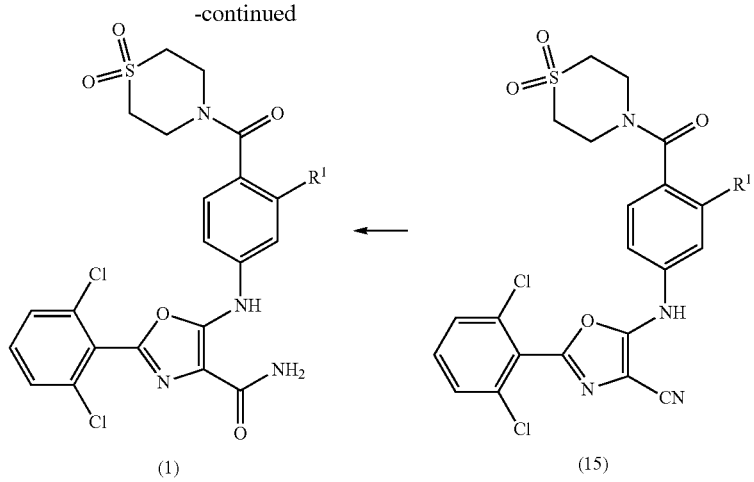

(1)  (15)

In the first step of the reaction sequence, 2,6-dichlorobenzoyl chloride (10) is reacted with aminomalononitrile (11) (e.g. the p-toluenesulfonate salt thereof) in a polar aprotic solvent such as N-methylpyrrolidone (NMP) to give the amino-oxazole nitrile (12). The reaction is typically conducted at an elevated temperature, for example in the range from 90° C. to 115° C.

The amino-oxazole nitrile (12) is converted to the corresponding bromo-compound (13) by a metal-free Sandmeyer procedure using tertiary butyl nitrite as a diazotizing agent in the presence of a halogen-donating compound such as bromo-(trimethyl)silane in dibromomethane. The reaction is typically carried out under a protective (e.g. nitrogen) atmosphere at a temperature of about 0° C.

The bromo-compound (13) is reacted with the substituted aniline (14) in a Buchwald-Hartwig palladium catalysed amination procedure to give the cyano-intermediate (15). The reaction makes use of a palladium(0) catalyst such as bis(dibenzylideneacetone)-palladium(0) (Pd(dba)$_2$) in a polar aprotic solvent such as dioxane in the presence of a suitable phosphine ligand such as 1,1'-ferrocenediyl-bis(diphenyl-phosphine) (dppf) or (5-diphenyl-phosphanyl-9,9-dimethyl-xanthen-4-yl)-diphenyl-phosphane, and a base such as potassium carbonate or caesium carbonate. The reaction is typically carried out at an elevated temperature (for example from 95-125° C.), for example in a sealed tube, using microwave heating.

The cyano-intermediate (15) is hydrolysed under mild acidic conditions (for example using sulphuric acid at a temperature of around 0° C.) to give the compound of formula (1).

Methods for making the compounds of formula (1) and key synthetic intermediates, as well as novel synthetic intermediates per se, form another aspect of the invention. Accordingly, in further embodiments (Embodiments 3.1 to 3.5), the invention provides:

3.1. A method for the preparation of a compound of formula (1) as defined herein, which method comprises the hydrolysis of a compound of formula (15):

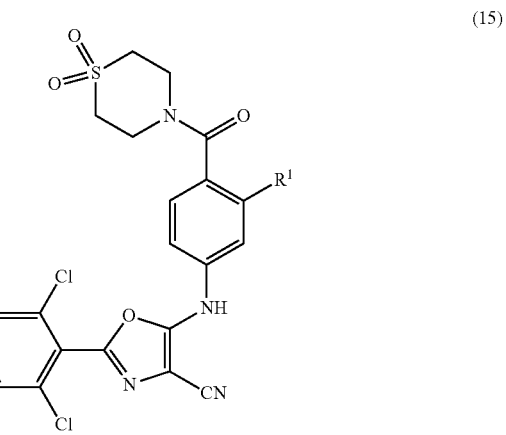

(15)

wherein R$^1$ is as defined herein, under acidic conditions (for example using sulphuric acid).

3.2 A method for the preparation of a compound of the formula (15) as defined herein, which method comprises the reaction of a compound of the formula (13) with a compound of the formula (14):

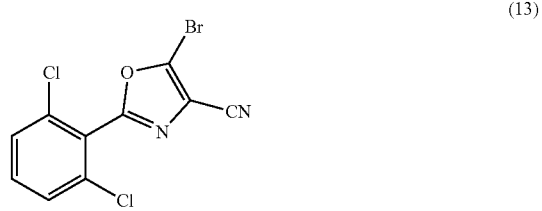

(13)

-continued (14)

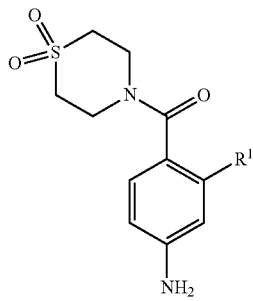

in the presence of a palladium (0) catalyst (such as Pd(dba)2, a phosphine ligand (such as DPPF), and a base (such as potassium carbonate.

3.3 A novel synthetic intermediate compound of formula (15) herein.

3.4 A novel synthetic intermediate according to Embodiment 3.3 wherein $R^1$ is hydrogen.

3.5 A novel synthetic intermediate according to Embodiment 3.3 wherein $R^1$ is fluorine.

Pharmaceutical Formulations

While it is possible for the active compound to be administered alone, it is preferable to present it as a pharmaceutical composition (e.g. formulation) comprising at least one active compound of the invention together with one or more pharmaceutically acceptable excipients such as carriers, adjuvants, diluents, fillers, buffers, stabilisers, preservatives, lubricants, or other materials well known to those skilled in the art, and optionally other therapeutic or prophylactic agents.

The term "pharmaceutically acceptable" as used herein refers to compounds, materials, compositions, and/or dosage forms which are, within the scope of sound medical judgment, suitable for use in contact with the tissues of a subject (e.g. human) without excessive toxicity, irritation, allergic response, or other problems or complication, commensurate with a reasonable benefit/risk ratio. Each excipient must also be "acceptable" in the sense of being compatible with the other ingredients of the formulation.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formulae (1), (2) and (3), or their pharmaceutically acceptable salts, can be formulated in accordance with known techniques, see for example, Remington's Pharmaceutical Sciences, Mack Publishing Company, Easton, PA, USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable cross-linked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively releasing the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastro-intestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Compositions for parenteral administration may be formulated for administration as discrete dosage units or may be formulated for administration by infusion.

Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 0.1 milligrams to 2 grams of active ingredient, more usually from 10 milligrams to 1 gram, for example, 50 milligrams to 500 milligrams.

The active compound will be administered to a patient in need thereof (for example a human or animal patient) in an amount sufficient to achieve the desired therapeutic effect.

Methods of Treatment

It is envisaged that the compounds of the formulae (1), (2) and (3) as defined in any one of Embodiments 1.1 to 1.9 will be useful in the prophylaxis or treatment of inflammatory diseases or conditions, immunological diseases or conditions, allergic diseases or disorders, transplant rejections and Graft-versus host disease. Examples of such disease states and conditions are set out above.

The compounds will typically be administered in amounts that are therapeutically or prophylactically useful and which generally are non-toxic. However, in certain situations (for example in the case of life threatening diseases), the benefits of administering a compound of the formula (1), (2) or (3) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

The compound of formula (1), (2) or (3) will generally be administered to a subject in need of such administration, for example a human patient.

A typical daily dose of the compound can be up to 1000 mg per day, for example in the range from 0.01 milligrams to 10 milligrams per kilogram of body weight, more usually from 0.025 milligrams to 5 milligrams per kilogram of body weight, for example up to 3 milligrams per kilogram of bodyweight, and more typically 0.15 milligrams to 5 milligrams per kilogram of bodyweight although higher or lower doses may be administered where required.

By way of example, an initial starting dose of 12.5 mg may be administered 2 to 3 times a day. The dosage can be increased by 12.5 mg a day every 3 to 5 days until the maximal tolerated and effective dose is reached for the individual as determined by the physician.

Ultimately, the quantity of compound administered will be commensurate with the nature of the disease or physiological condition being treated and the therapeutic benefits and the presence or absence of side effects produced by a given dosage regimen, and will be at the discretion of the physician.

The compounds of the formulae (1), (2) and (3) can be administered as the sole therapeutic agent or they can be administered in combination therapy with one or more other compounds such as steroids, interferons, apremilast (for psoriasis) or methotrexate (for rheumatoid arthritis).

Methods of Diagnosis

Prior to administration of a compound of the invention, a patient may be screened to determine whether a disease or condition from which the patient is or may be suffering is one which would be susceptible to treatment with a compound having activity against TYK2.

Accordingly, in further embodiments (4.1 to 4.3), the invention provides:

4.1 A compound of any one of Embodiments 1.1 to 1.9 for use in the treatment or prophylaxis of a disease state or condition in a patient who has been screened and has been determined as suffering from, or being at risk of suffering from, a disease or condition which would be susceptible to treatment with a compound having activity against a TYK2 kinase.

4.2 The use of a compound of any one of Embodiments 1.1 to 1.9 for the manufacture of a medicament for the treatment or prophylaxis of a disease state or condition in a patient who has been screened and has been determined as suffering from, or being at risk of suffering from, a disease or condition which would be susceptible to treatment with a compound having activity against TYK2 kinase.

4.3 A method for the diagnosis and treatment of a disease state or condition mediated by TYK2 kinase, which method comprises (i) screening a patient to determine whether a disease or condition from which the patient is or may be suffering is one which would be susceptible to treatment with a compound having activity against the kinase; and (ii) where it is indicated that the disease or condition from which the patient is thus susceptible, thereafter administering to the patient an effective TYK2 inhibiting amount of a compound of any one of Embodiments 1.1 to 1.9.

A subject (e.g. patient) may be subjected to a diagnostic test to detect a marker indicative of the presence of a disease or condition in which TYK2 is implicated, or a marker indicative of susceptibility to the said disease or condition. For example, subjects may be screened for genetic markers indicative of a susceptibility to develop an autoimmune or inflammatory disease.

The genetic marker can comprise a particular allele or single nucleotide polymorphism of the TYK2 gene which is indicative of susceptibility to an autoimmune disease such as multiple sclerosis (see for example Ban et al., *European Journal of Human Genetics* (2009), 17, 1309-1313) or an inflammatory bowel disease such as Crohn's disease (see Sato et al., *J. Clin. Immunol.* (2009), 29:815-825). The genetic marker can, for example, be a single nucleotide polymorphism in the TYK2 gene, or it can be a haplotype comprising a single nucleotide polymorphism in the TYK2 gene and a polymorphism in another gene.

The diagnostic tests are typically conducted on a biological sample selected from blood samples, biopsy samples, stool biopsies, sputum, chromosome analysis, pleural fluid, peritoneal fluid, or urine.

Methods of identifying genetic markers such as single nucleotide polymorphisms are well known. Examples of suitable methods for identifying such markers are described in Ban et al. and Sato et al. above.

EXAMPLES

The invention will now be illustrated, but not limited, by reference to the specific embodiments described in the following examples.

Abbreviations

In the Examples below, the following abbreviations are used:

ACN acetonitrile
DCM dichloromethane
DMF dimethylformamide
DPPF 1,1'-bis(diphenylphosphino)ferrocene
EDCl N-ethyl-N'-(3-dimethylaminopropyl)carbodiimide
$Et_3N$ triethylamine EtOAc ethyl acetate
HOBt hydroxybenzotriazole
HPLC high performance liquid chromatography
LCMS liquid chromatography-mass spectrometry
MeCN acetonitrile
MeOH methanol
mL millilitres
mmol millimoles
NMP N-methylpyrrolidone
Pd(dba)$_2$ bis(dibenzylideneacetone)palladium(0)
SiO$_2$ silica
tert-BuONO tertiary butyl nitrite
TFA trifluoroacetic acid
TLC thin layer chromatography Analytical Conditions NMR spectra were recorded on a Bruker 400 MHz instrument.

HPLC separations were carried out using Phenomenex LUNA-C18(2) 5p particle size, 2×50 mm columns.

Example 1

2-(2,6-dichlorophenyl)-5-[4-(1,1-dioxo-1,4-thiazinane-4-carbonyl)anilino-oxazole-4-carboxamide

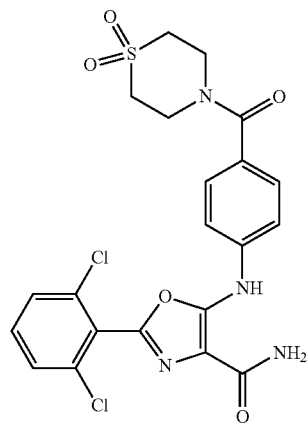 [SMILES: NC(=O)c1nc(-c2c(Cl)cccc2Cl)oc1Nc1ccc(C(=O)N2CCS(=O)(=O)CC2)cc1]

1A. Preparation of 5-amino-2-(2,6-dichlorophenyl)-oxazole-4-carbonitrile

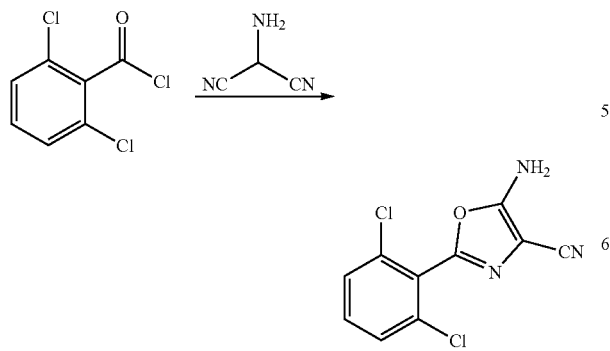

2,6-Dichlorobenzoyl chloride (10 g, 47.74 mmol) was added slowly to a solution of aminomalononitrile p-toluene-sulfonate (13.3 g, 52.51 mmol) in NMP (50 mL). The reaction mixture was heated at 110° C. for 14 hours before quenching with water (100 mL) and the resulting solid was collected by filtration. The crude product was dissolved in ethyl acetate (100 mL) and washed with water (40 mL×2), and the organic layer was dried over Na$_2$SO$_4$. The solvent was removed to give the title compound (19 g, crude) as a white solid.

$^1$H NMR (400 MHz, CDCl$_3$): δ: 7.37-7.35 (m, 2H), 7.29-7.26 (m, 1H), 6.19 (s, 2H).

1B. Preparation of 5-bromo-2-(2,6-dichlorophenyl)-oxazole-4-carbonitrile

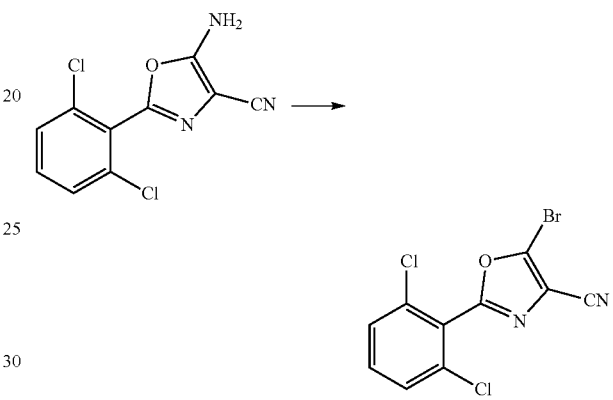

To a solution of 5-amino-4-cyano-2-(2,6-dichlorophenyl)-oxazole (9.0 g, 35.42 mmol) in CH$_2$Br$_2$ (50 mL) was added bromo(trimethyl)silane (13.56 g, 88.55 mmol). tert-BuONO (36.53 g, 354.20 mmol) was then added very slowly at 0° C. under a protective N$_2$ atmosphere and the mixture was stirred at 0° C. for 2.5 hour. The reaction mixture was then concentrated under reduced pressure to remove CH$_2$Br$_2$, water (H$_2$O 100 mL) was added and the resulting mixture was extracted with DCM (100 mL×3). The combined organic layers were dried over Na$_2$SO$_4$, filtered and concentrated under reduced pressure to give a residue which was purified by column chromatography (SiO$_2$, petroleum ether/ethyl acetate=50/1 to 10:1). The title compound (8 g, 71.03% yield) was obtained as a white solid.

1C. Preparation of 4-(4-nitrobenzoyl)-1,1-dioxo-1,4-thiazinane

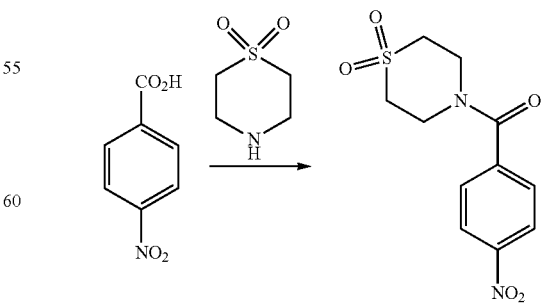

To a mixture of 4-nitrobenzoic acid (5 g, 29.92 mmol) and 1,4-thiazinane 1,1-dioxide hydrochloride (5.1 g, 29.92 mmol) in DMF (50 mL) was added HOBt (6.1 g, 44.88 mmol), EDCl (8.6 g, 44.88 mmol), Et₃N (6.1 g, 59.84 mmol) in one portion at 15° C. under N₂. The mixture was stirred at 15° C. for 14 hours. The reaction mixture was diluted with saturated Na₂CO₃ (300 mL) and extracted with EtOAc (150 mL×3). The combined organic layers were dried over Na₂SO₄, filtered and concentrated under reduced pressure to give the title compound (6.5 g, crude) as a white solid.

¹H NMR (400 MHz, CDCl₃): δ: 8.27 (d, J=8.8 Hz, 2H), 7.55 (d, J=8.8 Hz, 2H), 4.33-3.75 (m, 4H), 3.22-2.75 (m, 4H).

1D. Preparation of 4-(4-aminobenzoyl)-1,1-dioxo-1,4-thiazinane

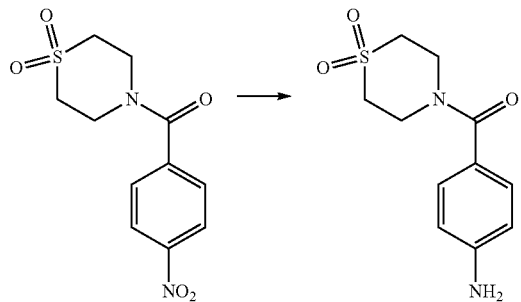 [SMILES: O=C(c1ccc([N+](=O)[O-])cc1)N1CCS(=O)(=O)CC1 ; Nc1ccc(C(=O)N2CCS(=O)(=O)CC2)cc1]

To a solution of 4-(4-nitrobenzoyl)-1,1-dioxo-1,4-thiazinane (5.5 g, 19.35 mmol) in MeOH (100 mL) was added Pd/C (1.0 g, 19.35 mmol) under N₂. The suspension was degassed under vacuum and purged with H₂ several times, and then stirred under H₂ (15 psi) at 15° C. for 14 hours. The reaction mixture was filtered and the filtrate was concentrated to give the title compound (4.5 g, 91.45% yield) as a white solid.

1H NMR (400 MHz, (CDCl3): δ: 7.36-7.26 (m, 2H), 6.80-6.61 (m, 2H), 4.26-4.08 (m, 4H), 4.06-3.88 (m, 2H), 3.21-2.95 (m, 4H)

1E. Preparation of 2-(2,6-dichlorophenyl)-5-[4-(1,1-dioxo-1,4-thiazinane-4-carbonyl)anilino]oxazole-4-carbonitrile

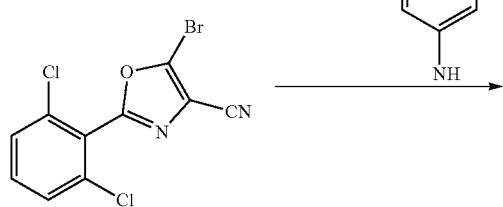

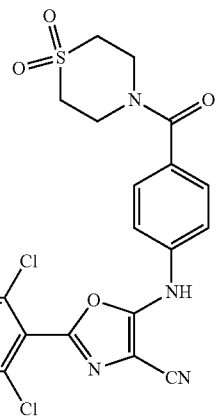

1,4-Dioxane (13 mL) was added to a mixture of 5-bromo-4-cyano-2-(2,6-dichlorophenyl)-oxazole (500 mg, 1.57 mmol), 4-(4-aminobenzoyl)-1,1-dioxo-1,4-thiazinane (399.25 mg, 1.57 mmol) and Pd(dba)₂ (90.28 mg, 157 μmol), DPPF (130.56 mg, 235.5 μmol), K₂CO₃ (976.45 mg, 7.07 mmol) in a reaction tube which was sealed and subjected to microwave heating at 120° C. for 4 hours. The resulting reaction mixture was filtered and concentrated in vacuum, and water (30 mL) was added before extracting with DCM (50 mL×3). The combined organic phases were dried over Na₂SO₄, filtered and concentrated under reduced pressure to give a residue which was purified by column chromatography (SiO₂, petroleum ether/ethyl acetate=10/1 to 2/3). The title compound (110 mg, 14.26% yield) was obtained as a brown solid.

1F. Preparation of (2,6-dichlorophenyl)-5-[4-(1,1-dioxo-1,4-thiazinane-4-carbonyl)anilino]oxazole-4-carboxamide

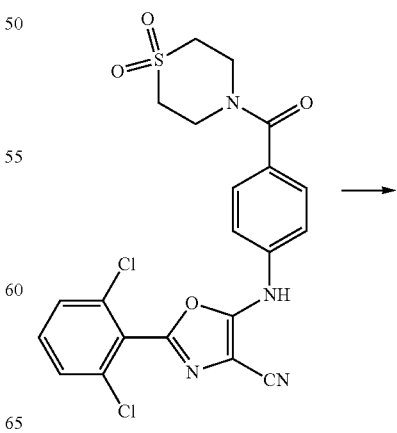

23

-continued

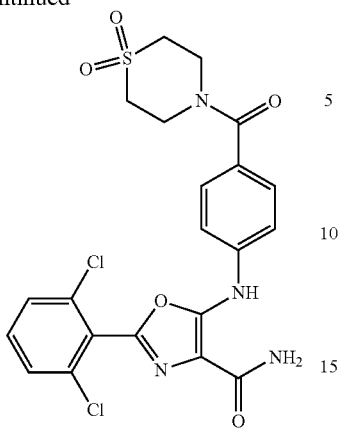

A mixture of 2-(2,6-dichlorophenyl)-5-[4-(1,1-dioxo-1,4-thiazinane-4-carbonyl)anilino]oxazole-4-carbonitrile (100 mg, 203.52 umol) in $H_2SO_4$ (1 mL) at 0° C. was stirred at 15° C. for 2 hour under an $N_2$ atmosphere. LCMS analysis after this time indicated that the reaction had gone to completion and so the reaction mixture was quenched with ice at 0° C., and then filtered. The filtrate was extracted with EtOAc (30 mL: 10 mL×3), and the combined organic layers were dried over $Na_2SO_4$, filtered and concentrated under reduced pressure to give a residue which was purified by preparative HPLC (TFA conditions). The title compound, (2,6-dichlorophenyl)-5-[4-(1,1-dioxo-1,4-thiazinane-4-carbonyl)-anilino]oxazole-4-carboxamide (25 mg, 24% yield, 99.61% purity), was obtained as a yellow solid.

1H NMR (400 MHz, (CDCl$_3$): δ:9.05 (s, 1H), 7.50-7.48 (m, 2H), 7.46-7.44 (m, 3H), 7.41-7.38 (m, 2H), 6.50 (s, 1H), 5.38 (s, 1H), 4.12 (s, 4H), 3.07 (s, 4H).

MS (ESI): mass calcd. for C21H18 Cl 2N4O5S 508.0408.04, m/z found, 509.0 [M+H]+.

Example 2

2-(2,6-dichlorophenyl)-5-|3-fluoro-4-(1,1-dioxo-1,4-thiazinane-4-carbonyl)anilino]-oxazole-4-carboxamide

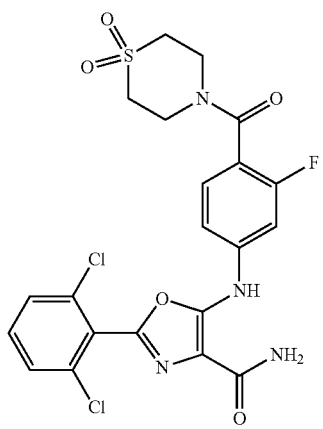 [SMILES: NC(=O)c1nc(-c2c(Cl)cccc2Cl)oc1Nc1ccc(C(=O)N2CCS(=O)(=O)CC2)c(F)c1]

24

2A. Preparation of 4-(2-fluoro-4-nitrobenzoyl)-1,1-dioxo-1,4-thiazinane

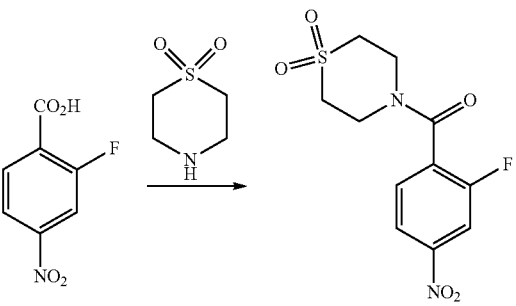

To a mixture of 2-fluoro-4-nitrobenzoic acid (5 g, 27 mmol) and 1,4-thiazinane 1,1-dioxide (5.1 g, 29.7 mmol, HCl) in DMF (50 mL) was added HOBt (5.47 g, 40.5 mmol), EDCl (7.77 g, 40.5 mmol) and Et$_3$N (5.47 g, 54 mmol) in one portion at 15° C. under $N_2$. The resulting mixture was stirred at 15° C. for 14 hours, after which TLC (petroleum ether:ethyl acetate=1:1, R$_f$=0.1) indicated that the carboxylic acid starting material had been completely consumed and one new spot had formed, thereby indicating that a clean conversion to the desired product had occurred. The reaction mixture was then diluted with saturated Na$_2$CO$_3$ (300 mL) and extracted with EtOAc (150 mL×3). The combined organic layers were dried over Na$_2$SO$_4$, filtered and concentrated under reduced pressure to give the title compound (7 g, crude) as a yellow solid.

$^1$H NMR: 400 MHz CDCl$_3$: δ 8.17 (d, J=8.0 Hz, 1H), 8.06 (d, J=8.4 Hz, 1H), 7.67-7.63 (m, 1H), 4.32 (s, 2H), 3.82 (s, 2H), 3.21 (s, 2H), 3.11 (s, 2H).

2B. Preparation of 4-(2-fluoro-4-aminobenzoyl)-1,1-dioxo-1,4-thiazinane

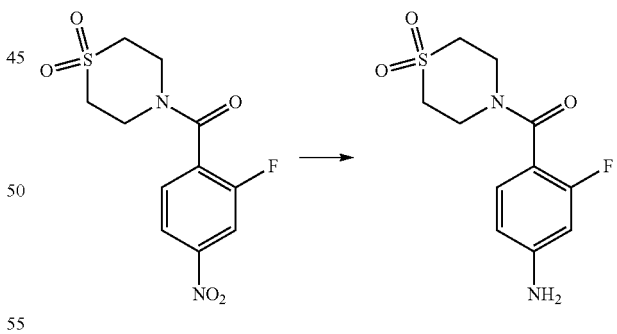

To a solution of 4-(2-fluoro-4-nitrobenzoyl)-1,1-dioxo-1,4-thiazinane (7 g, 23.2 mmol) in MeOH (100 mL) was added Pd/C (3 g, 10% purity). The suspension was degassed under vacuum and purged with H$_2$ several times. The mixture was then stirred under H$_2$ (15 psi) at 15° C. for 12 hours by after which time TLC (petroleum ether/ethyl acetate=1/1, R$_f$=0.3) indicated that the nitro-phenyl starting compound had been completely consumed and one new product spot had formed. The reaction mixture was filtered and concentrated under reduced pressure to give the title compound (5 g, crude) as a yellow solid.

$^1$H NMR: 400 MHz CDCl$_3$: δ 7.16-7.12 (m, 1H), 6.43-6.41 (m, 1H), 6.31-6.27 (m, 1H), 4.35 (s, 2H), 4.11-3.86 (m, 4H), 3.10 (s, 4H)

2C. Preparation of 2-(2,6-dichlorophenyl)-5-[3-fluoro-4-(1,1-dioxo-1,4-thiazinane-4-carbonyl)anilino]oxazole-4-carbonitrile

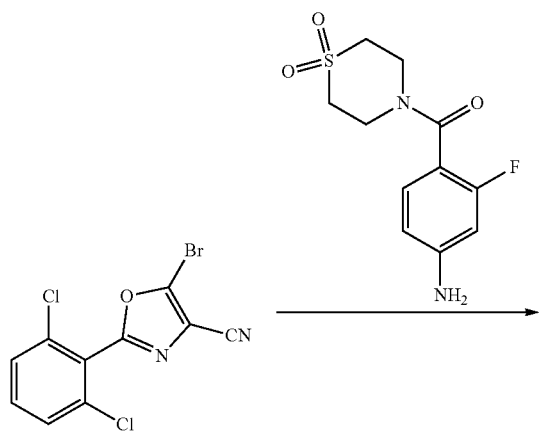

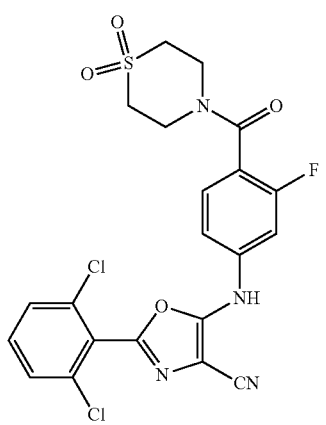

To a solution of 5-bromo-2-(2,6-dichlorophenyl)-oxazole-4-carbonitrile (2 g, 6.29 mmol) (Example 1A) in 1,4-dioxane (40 mL) was added 4-(2-fluoro-4-aminobenzoyl)-1,1-dioxo-1,4-thiazinane (1.88 g, 6.92 mmol), Cs$_2$CO$_3$ (4.10 g, 12.6 mmol), and (5-diphenyl-phosphanyl-9,9-dimethyl-xanthen-4-yl)-diphenyl-phosphane (364 mg, 629 μmol). The suspension was degassed under vacuum and purged with N$_2$ several times. Then (1E,4E)-1,5-diphenylpenta-1,4-dien-3-one:palladium (288 mg, 315 μmol) was added and purged with N$_2$ several times. The reaction mixture was heated to 100° C. and stirred for 12 hours after which time TLC (petroleum ether/ethyl acetate=1/1, R$_f$=0.9) indicated that the bromo-cyano-oxazole had been completely consumed and that one new product spot had formed, thereby indicating that the reaction had resulted in a clean conversion to the desired product. The reaction mixture was filtered and the filter cake was washed with EtOAc (300 mL). The filtrate was then concentrated to give crude product which was purified by column chromatography (SiO$_2$, petroleum ether/ethyl acetate=20/1 to 0:1) to give the title compound (1.1 g, 2.16 mmol, 34.3% yield) as yellow solid.

2D. Preparation of (2,6-dichlorophenyl)-5-[3-fluoro-4-(1,1-dioxo-1,4-thiazinane-4-carbonyl)anilino]oxazole-4-carboxamide

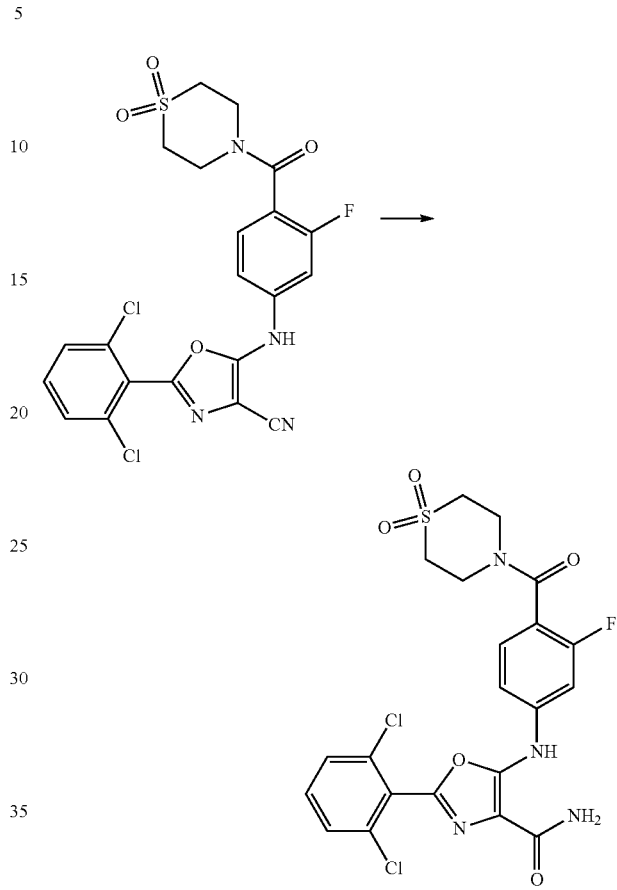

A mixture of 2-(2,6-dichlorophenyl)-5-[2-fluoro-4-(1,1-dioxo-1,4-thiazinane-4-carbonyl)anilino]oxazole-4-carbonitrile (0.2 g, 393 μmol) in H$_2$SO$_4$ (2 mL) was degassed and purged with N$_2$ 3 times, and then the mixture was stirred at 20° C. for 1 hour under an N$_2$ atmosphere after which time HPLC and LCMS analysis showed that the starting material had been completely consumed. The residue was poured into ice H$_2$O 50 mL and extracted with EtOAc 60 mL (20 mL×3). The combined organic layers were dried over Na$_2$SO$_4$, filtered and concentrated under reduced pressure to give a residue which was purified by prep-HPLC (column: Phenomenex luna C$_{18}$ 250×50 mm 10 μm: mobile phase: [water (0.1% TFA-ACN]; B %: 20%-50%, 20 minutes) to give a crude product. The crude product was treated with NaHCO$_3$ (aq), extracted with DCM (20 mL), dried and concentrated, then dissolved in MeCN/water to freeze drying to give the title compound (60.3 mg, 113 umol, 28.8% yield, 98.9% purity) as yellow solid.

$^1$H NMR: 400 MHz CDCl$_3$: δ 9.11 (s, 1H), 7.51-7.42 (m, 4H), 7.18-7.14 (m, 1H), 7.14-7.12 (m, 1H), 6.54 (s, 1H), 5.45 (s, 1H), 4.27 (s, 2H), 3.87 (s, 2H), 3.17-3.06 (m, 4H).

Example 3

Biological Activities
(i) TYK2 and JAK Kinase Inhibition Assays
The compounds of the invention were assayed for their ability to inhibit TYK2 kinase and other JAK kinases. The activities of the compounds were compared with the activities of Compound A (2-(2-chloro-6-fluoro-phenyl)-5-[4-(morpholine-4-carbonyl)-phenylamino]-oxazole-4-carboxylic acid amide) and Compound B (2-(2,6-dichloro-phenyl)-5-[4-(morpholine-4-carbonyl)-phenylamino]-oxazole-4-carboxylic acid amide):

which are the compounds of Examples 25 and 29 respectively in each of WO 2015/032423 and WO2018/073438.

Substrates and kinases used in the assays are identified in Table 2 below.

Kinase assays were performed at Reaction Biology Corp., Malvern, Pennsylvania, USA, using the general procedure set out below. In the assays, the ATP concentration was 100 µM and the top compound concentrations were 10 µM.

Note that the TYK2 and JAK kinase data in Table 7 on page 61 of WO 2015/032423 were generated using an assay in which the ATP concentration was 10 µM whereas, as indicated above, the assay described in the protocol below used an ATP concentration of 100 µM.

Compound A

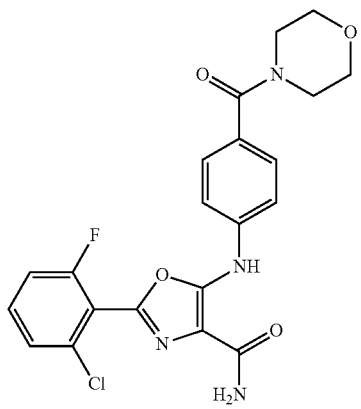

Compound B

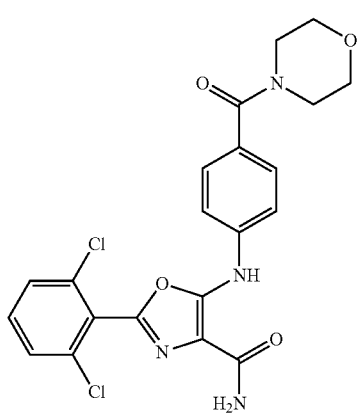

Assay:
1) Prepare indicated substrate in freshly prepared Base Reaction Buffer (20 mM Hepes pH 7.5, 10 mM MgCl$_2$, 1 mM EGTA, 0.02% Brij35, 0.02 mg/ml BSA, 0.1 mM Na$_3$VO$_4$, 2 mM DTT, 1% DMSO).
2) Deliver cofactors (1.5 mM CaCl$_2$, 16 µg/mL Calmodulin, 2 mM MnCl$_2$) to the substrate solution above
3) Deliver indicated kinase into the substrate solution and gently mix
4) Deliver varying concentrations of test compound in DMSO into the kinase reaction mixture
5) Deliver $^{33}$P-ATP (specific activity 0.01 µCi/µL final) into the reaction mixture to initiate the reaction
6) Incubate kinase reaction for 120 min at room temperature
7) Reactions are spotted onto P81 ion exchange filter paper (Whatman #3698-915)
8) Unbound phosphate is removed by washing filters extensively in 0.75% Phosphoric acid.
9) $^{33}$P signal was determined using Typhoon phosphorimagers (GE Healthcare). After subtraction of background derived from control reactions containing inactive enzyme, IC$_{50}$ values were determined using the non-linear regression function in Prism (Graphpad software).

TABLE 2

| Protein Name | HUGO symbol | Substrate | Genbank Accession # | Protein Accession # | Clone | Expression | Tag |
|---|---|---|---|---|---|---|---|
| JAK1 | JAK1 | pEY | NP_002218.2 | P23458 | aa 866-1154 | Baculovirus in Sf21 insect cells | N-terminal GST tag |
| JAK2 | JAK2 | pEY | NP_004963 | O60674 | aa 809-1132 +g | Baculovirus in Sf21 insect cells | N-terminal GST tag |
| JAK3 | JAK3 | JAK3tide | NP_000206 | P52333 | aa 781-1124 | Baculovirus in Sf21 insect cells | N-terminal GST tag |
| TYK2 | TYK2 | AXLtide | NP_003322.2 | P29597 | Aa 833-1187 | Baculovirus in Sf21 insect cells | N-terminal GST tag |

Substrates:
AXLtide = [KKSRGDYMTMQIG]
JAK3tide = [Ac-GEEEEYFELVKKKK-NH$_2$]
pEY = poly Glu-Tyr [Glu:Tyr (4:1), M.W. = 5,000-20,000]

The results are shown in Table 3 below.

TABLE 3

| | IC$_{50}$ (nM) | | | | Selectivity v TYK2 | | | |
|---|---|---|---|---|---|---|---|---|
| | TYK2 | JAK1 | JAK2 | JAK3 | TYK2 | JAK1 | JAK2 | JAK3 |
| Comparative Compound A | 10 | 49 | 87 | 290 | 1 | 4.9 | 8.7 | 29 |
| Comparative Compound B | 5.1 | 26 | 77 | 271 | 1 | 5.1 | 15.1 | 53.1 |
| Compound (2) - Example 1 | 1.9 | 20 | 50 | 212 | 1 | 10.5 | 26.3 | 111.6 |
| Compound (3) - Example 2 | 4.7 | 51 | 153 | 772 | 1 | 10.9 | 32.5 | 164.3 |

Although all tested compounds were shown to possess good TYK2 inhibitory activity, the data illustrate that the compounds of the invention (Compounds (2) and (3)) are both more potent and more selective with respect to TYK2 (particularly towards TYK2 over JAK2 and JAK3) than the prior art compounds A and B.

(ii) Cytochrome P450 Inhibition Assays

The susceptibility of Compounds (2) and (3) to potential drug-drug interactions was tested by assaying their abilities to inhibit various cytochrome P450 isoforms. Prior art Compound B (see Example 3 above) was also tested as a comparative example.

Test compounds, prepared and serially diluted in DMSO, were incubated at six concentrations (1% DMSO final) with pooled human liver microsomes in the presence of probe substrate for each isoform, and their effects on the metabolism of probe substrates determined. Incubations (in 96-well plates) were carried out at 37° C. in 0.1 M Tris buffer, pH 7.4, with reactions initiated by the addition of cofactor, NADPH (1 mM final concentration).

At the specified times, reactions were terminated with acetonitrile containing an analytical internal standard, samples were centrifuged and the supernatant fractions were analysed for probe substrate metabolites by mass spectrometry (LC-MS/MS). The instrument responses were normalised to internal standard and compared to the appropriate solvent controls to determine the amount of metabolite formed from the probe substrates relative to these "uninhibited" controls.

The results are reported as percentage inhibition and IC$_{50}$ values (concentration resulting in a 50% reduction in probe metabolite formation) were calculated using a non-linear sigmoidal dose response equation (BioBook):

% inhibition=lowest value+(highest value−lowest value)/(1+10^((Log IC$_{50}$−X)*HillSlope))

where X=Log concentration.

The CYP450 isoforms studied, and their respective probe substrates are shown in Table 4.

TABLE 4

| CYP450 isoform | Substrate |
|---|---|
| CYP1A2 | Phenacetin |
| CYP2B6 | Bupropion |
| CYP2C8 | Amodiaquine |
| CYP2C9 | Diclofenac |
| CYP2C19 | S-(+)-Mephenytoin |
| CYP2D6 | Dextromethorphan |
| CYP3A4 | Midazolam |
| CYP3A4 | Testosterone |

The assay results are shown in Table 5.

TABLE 5

| Compound | CYP1A2 | CYP2B6 | CYP2C8 | CYP2C19 | CYP2C9 | CYP2D6 | CYP3A4 (MID) | CYP3A4 (Test) |
|---|---|---|---|---|---|---|---|---|
| Comparative Compound B | >30 | >30 | >8.2 | >30 | 4.4 | >30 | >30 | >30 |
| Compound (2) | >30 | >30 | >30 | >30 | 26 | >30 | >30 | >30 |
| Compound (3) | >30 | >30 | >30 | 29 | >30 | >30 | >30 | >30 |

Although all tested compounds show good CYP inhibition profiles, the data illustrate that the compounds of the invention (Compounds (2) and (3)) have better CYP inhibition profiles (i.e. inhibit the CYP isoforms tested to a lesser extent) than the Comparative Compound B, particularly with respect to CYP2C8 and CYP2D6.

(iii) hERG Channel Inhibition Assay

The potential for compounds to inhibit the hERG potassium channel was determined using a hERG-HEK stably transfected cell line on the Sophion Qube automated electrophysiology platform. The assay was performed at room temperature and recordings of the hERG tail current from individual cells was made using single-hole QChips.

The potency (IC$_{50}$) of test compounds to inhibit the hERG channel was determined from a concentration-response curve generated from 8 test compound concentrations with up to 4 replicates per concentration.

The compound concentration was added to the test well twice to ensure complete exchange of the external buffer with the test compound. In total, compound was applied to the well for >7 minutes.

Results are shown in Table 6 below.

TABLE 6

| Compound | IC$_{50}$ (uM) | Max Conc. (uM) | % inhibition at Max. Conc. |
|---|---|---|---|
| Comparative Compound B | ~30 | 30 | 50.5 |
| Compound (2) | >30 | 30 | 38.6 |
| Compound (3) | >30 | 30 | 31.5 |

All three tested compounds show relatively low hERG activity, but the results demonstrate that the compounds of the invention (Compound (2) and Compound (3)) have an even lower hERG liability compared to prior art comparative Compound B.

(iv) Hepatocyte Stability Assay

The compounds (2) and (3) of the invention and prior art comparative Compound B were tested in hepatocyte stability assays which were performed using pooled hepatocytes from mouse (male CD-1), rat (male Sprague-Dawley), dog (male Beagle) and human (mixed gender). Test and control compounds were incubated with hepatocytes at 37° C. Aliquots were removed at 6 timepoints over a one hour period. Samples were centrifuged and the supernatant fractions analysed for parent compound by mass spectrometry (LC-MS/MS).

The amount of compound remaining (expressed as %) was determined from the MS response in each sample relative to that in the T=0 samples, and used to determine the half-life and intrinsic clearance of the compound.

Results are shown in Table 7 below.

TABLE 7

| | Mouse | | Rat | | Dog | | Human | |
|---|---|---|---|---|---|---|---|---|
| Compound | CL$_{int}$ µL/min/10$^6$ cells | T$_{1/2}$ mins. | CL$_{int}$ µL/min/10$^6$ cells | T$_{1/2}$ mins. | CL$_{int}$ µL/min/10$^6$ cells | T$_{1/2}$ mins. | CL$_{int}$ µL/min/10$^6$ cells | T$_{1/2}$ mins. |
| Comparative Compound B | 40.5 | 27 | 103.7 | 14.8 | 29.8 | 53.5 | 9.0 | 124 |
| Compound (2) | 16.8 | 65.3 | 50.0 | 30.6 | <3.0 | >460 | <3.0 | >460 |
| Compound (3) | 28.0 | 39.2 | 53.8 | 28.5 | 8.8 | 184.9 | 4.2 | 335 |

While comparative Compound B exhibits a good half-life in humans (over 2 hours), the data in Table 7 indicate that compounds (2) and (3) of the invention have a significantly reduced rate of clearance in all four hepatocyte stability assays compared to prior art comparative Compound B and that, consequently, the half life (T$_{1/2}$) of the compounds of the invention is even longer in all four assays than the half life of the comparative Compound B.

(v) pSTAT3 Inhibition

The compounds (2) and (3) of the invention and prior art comparative Compounds A and B were tested for pSTAT3 inhibition in response to IL-22 stimulation in serum starved HT29 cells.

HT29 cells were serum starved overnight before the four test compounds were diluted to generate a 9-point semi-log dose dilution with a top concentration of 10 µM, plus vehicle control. HT29 cells were incubated with the test compounds for 20 min at 37° C. HT29 cells were incubated for a further 15 min with 10 ng/ml human IL-22 before cells were fixed with 4% PFA for 10 min, and 90% methanol for 30 min before being labelled with a phospho-STAT3Y705 antibody (CST #9145). Cells were rinsed three times using 0.5% BSA/PBS solution before being incubated with Alexa-488 anti-rabbit secondary antibodies.

Mean fluorescence intensity of phospho-STAT3 in single cells was analysed by flow cytometry using an Intellicyt iQue instrument and FlowJo software. The IC50 was determined using a four-parameter analysis following removal of background signal and normalisation to the DMSO control.

Results are shown in Table 8 below.

TABLE 8

| Test Compound | IC$_{50}$(nM) | % pSTAT3 inhibition at 10 µM |
|---|---|---|
| Comparative Compound A | 170 | 96.9 |
| Comparative Compound B | 53 | 97.9 |
| Compound (2) | 16 | 95.9 |
| Compound (3) | 231.1 | 95.9 |

While Both Comparative Compound B and Compound (2) were Shown to have IC$_{50}$ Values Against pSTAT3 Inhibition of Less than 100 nM, the IC$_{50}$ Value for Compound (2) was Significantly Lower than for Comparative Compound B.

(vi) Human Primary CD4CD45RO+ Cells Assay

Inhibition of IL-17F production and STAT3 phosphorylation by Compounds (2) and (3) and Comparative Compound B were measured in Th17 cells derived from human peripheral blood CD4CD45RO+ cells.

Fresh human Peripheral blood CD4CD45RO+ cells were purchased commercially (Generon, UK); 3 separate vials from 3 different volunteers for experimental replicates. Cells were grown in T-cell medium (Thermo Fisher) containing 10 ng/ml recombinant human IL-1B (R&D Systems), IL-23 (R&D Systems), TGF-B1 (R&D Systems) and 50 ng/ml IL-6 (R&D Systems) together with anti-CD3/CD28 magnetic Dynabeads (Thermo Fisher). These were grown for 11 days to induce expansion of Th17 cells. Prior to plating for assays cells were grown overnight in T-cell medium supplemented with human serum (1%) overnight. Media was removed and replaced with unsupplemented RPMI for 4 h prior to assay.

To measure IL-17F levels, 200,000 cells were plated into a 96 well plate and preincubated with compounds for 30 minutes followed by stimulation with recombinant IL-23 at 6.25 ng/ml and recombinant human IL-1B at 0.1 ng/ml for 48 h. Supernatants were removed and IL-17F levels measured using a commercially available ELISA kit (Thermo Fisher; BMS2037-2).

To measure pSTAT3 levels, 200,000 cells were plated into a 96 well plate and preincubated with compounds for 30 minutes followed by stimulation with recombinant IL-23 at 12.5 ng/ml for 15 minutes then lysed using cell lysis buffer.

pSTAT3 levels in the lysates were measured using a commercially available ELISA kit (Thermo Fisher; 85-86102-11).

ELISAs were carried out according to manufacturers instructions and absorbance read using a microplate reader (Thermo Fisher; Varioskan). Data was normalised to the response in untreated samples using the formula:

% of control=((Stimulated sample Conc.−unstimulated sample Conc.)×100)/(Control stimulated Conc.−control unstimulated Conc.)

Graphpad Prism 8.1.0 was used to calculate I050 values using a Nonlinear 4 parameter logistic regression model (4PL).

The results are shown in Tables 9A and 9B below:

TABLE 9A

IL17-F Production Inhibition

| Compound | Donor 1 | Donor 2 | Donor 3 | Average (nM) | SD |
|---|---|---|---|---|---|
| Comparative Compound B | 243 | 217 | 148 | 203 | 49 |
| Compound (2) | 117 | 134 | 64 | 105 | 37 |
| Compound (3) | 57 | 548 | 105 | 237 | 271 |

TABLE 9B

Inhibition of STAT3 phosphorylation

| Compound | Donor 1 | Donor 2 | Donor 3 | Average (nM) | SD |
|---|---|---|---|---|---|
| Comparative Compound B | 111 | 17 | 54 | 61 | 47 |
| Compound (2) | 69 | 29 | 55 | 51 | 20 |
| Compound (3) | 157 | 29 | 91 | 92 | 64 |

While all tested compounds showed inhibition of IL17-F production and STAT3 phosphorylation, in both assays Compound (2) was shown to be more active than comparative Compound B and Compound (3).

Comparative Data—Conclusions

The data obtained from assays (i) to (vi) above indicate that the compounds of the invention have significant advantages over the structurally most similar compound (Compound B) in WO2015/032423.

Thus, both compounds (2) and (3) are more active than Compound B in the TYK2 kinase inhibition assay and both have greater selectivity for TYK2 versus JAK1, JAK2 and JAK3 kinases than Compound B.

Compounds (2) and (3) have slightly advantageous properties compared to prior art comparative Compound B in the cytochrome P450 assays, notably in the CYP2C8 and CYP2C9 assays.

Compounds (2) and (3) have a reduced hERG liability compared to prior art comparative Compound B.

In the hepatocyte stability assays, Compounds (2) and (3) showed a reduced rate of clearance and a consequently longer half life than comparative Compound B.

In addition, Compound (2) is more potent in inhibiting phosphorylation of STAT3 in IL-22 stimulated HT29 cells and Th17 cells compared to comparative Compound B.

Finally, Compound (2) shows a greater inhibition of IL-17F production in Th17 cells compared to comparative Compound B.

Taken together, the data indicate that Compounds (2) and (3) are highly potent and selective TYK2 kinase inhibitors and have excellent pharmacokinetic properties.

Example 4

Pharmaceutical Formulations
(i) Tablet Formulation

A tablet composition containing a compound of the formula (2) or formula (3) or a pharmaceutically acceptable salt thereof is prepared by mixing 50 mg of the compound with 197 mg of lactose (BP) as diluent, and 3 mg magnesium stearate as a lubricant and compressing to form a tablet in a known manner.

(ii) Capsule Formulation

A capsule formulation is prepared by mixing 100 mg of a compound of the formula (2) or formula (3) or a pharmaceutically acceptable salt thereof with 100 mg lactose and filling the resulting mixture into standard opaque hard gelatin capsules.

(iii) Sub-Cutaneous Injection Formulation

A composition for sub-cutaneous administration is prepared by mixing a compound of the formula (2) or formula (3) with pharmaceutical grade corn oil to give a concentration of 5 mg/mL. The composition is sterilised and filled into a suitable container.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound having the formula (1):

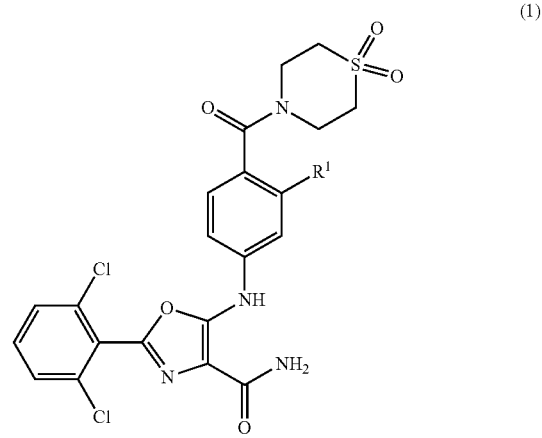

or being a salt or tautomer thereof; wherein $R^1$ is hydrogen or fluorine.

2. A compound according to claim 1, wherein $R^1$ is hydrogen; the compound having the formula (2):

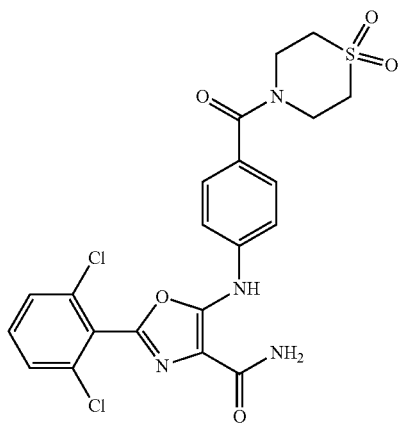

(2)

or being a salt or tautomer thereof.

3. A compound according to claim 1 wherein $R^1$ is fluorine; the compound having the formula (3):

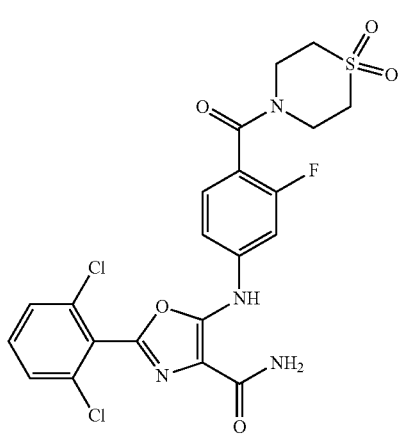

(3)

or being a salt or tautomer thereof.

4. A compound according to claim 1 which is a non-salt form.

5. A method of inhibiting a TYK2 kinase, which method comprises bringing into contact with the TYK2 kinase an effective TYK2 kinase-inhibiting amount of a compound according to claim 1.

6. A method of treating an inflammatory disorder, an immune disorder or an autoimmune disease, the method comprising administering to a subject in need thereof an effective amount of a compound according to claim 1.

7. A method according to claim 6 which is a method of treating an autoimmune disease.

8. A pharmaceutical composition comprising a compound as defined in claim 1 and a pharmaceutically acceptable excipient.

9. A method according to claim 5 wherein the inhibition of the TYK2 kinase takes place in vivo.

10. A compound according to claim 2 which is a non-salt form.

11. A compound according to claim 3 which is a non-salt form.

12. A method of inhibiting a TYK2 kinase, which method comprises bringing into contact with the TYK2 kinase an effective TYK2 kinase-inhibiting amount of a compound according to claim 2.

13. A method of treating an inflammatory disorder, an immune disorder or an autoimmune disease, the method comprising administering to a subject in need thereof an effective amount of a compound according to claim 2.

14. A method according to claim 12 wherein the inhibition of the TYK2 kinase takes place in vivo.

15. A pharmaceutical composition comprising a compound as defined in claim 2 and a pharmaceutically acceptable excipient.

16. A pharmaceutical composition comprising a compound as defined in claim 3 and a pharmaceutically acceptable excipient.

17. A pharmaceutical composition comprising a compound as defined in claim 4 and a pharmaceutically acceptable excipient.

18. A method for the preparation of a compound of formula (1) as defined in claim 1, which method comprises the hydrolysis of a compound of formula (15):

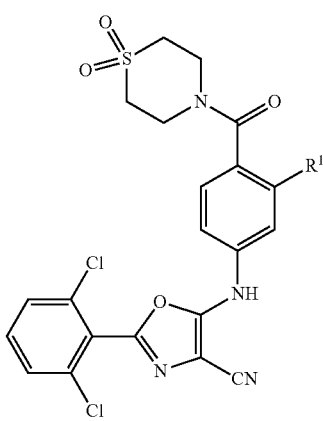

(15)

wherein $R^1$ is hydrogen or fluorine, under acidic conditions.

19. A method according to claim 18 wherein $R^1$ is hydrogen.

20. A method according to claim 18 wherein $R^1$ is fluorine.

* * * * *